(12) United States Patent
Greener

(10) Patent No.: US 6,635,457 B1
(45) Date of Patent: Oct. 21, 2003

(54) SELECTION FOR MORE EFFICIENT TRANSFORMATION HOST CELLS

(75) Inventor: Alan L. Greener, San Diego, CA (US)

(73) Assignee: Stratagene, La Jolla, CA (US)

( * ) Notice: Subject to any disclaimer, the term of this patent is extended or adjusted under 35 U.S.C. 154(b) by 0 days.

(21) Appl. No.: 09/625,595

(22) Filed: Jul. 26, 2000

Related U.S. Application Data

(60) Provisional application No. 60/146,516, filed on Jul. 30, 1999.

(51) Int. Cl.[7] .................. C12N 13/00; C12N 15/00; C12N 15/74; C12N 15/76; C12N 15/87
(52) U.S. Cl. .................. 435/173.8; 435/173.1; 435/440; 435/471; 435/455; 435/468; 435/252.1; 435/325; 435/410
(58) Field of Search .................. 435/173.8, 173.1, 435/440, 471, 455, 468, 252.1, 325, 410

(56) References Cited

U.S. PATENT DOCUMENTS

| | | | |
|---|---|---|---|
| 4,910,140 A | | 3/1990 | Dower .................. 435/488 |
| 5,703,219 A | * | 12/1997 | Thompson et al. |
| 6,010,613 A | * | 1/2000 | Walters et al. |

FOREIGN PATENT DOCUMENTS

| | | |
|---|---|---|
| WO | WO 96/07750 | 3/1996 |
| WO | WO 98/49266 | 11/1998 |
| WO | WO 99/11771 | 3/1999 |

OTHER PUBLICATIONS

Doran et al (1983) J. Bact. 155: 159–168.*
Sambrook et al (1989) Molecular Cloning, A Laboratory Manual, Cold Spring Harbor Laboratory Press, pp. 1.76–1.81.*
Peterfy et al., 1995, *Methods In Molecular And Cellular Biology*, 5:353–362.
Rahman et al., 1999, *Journal of Bacteriology*, 181:1515–1523.
Thompson et al., 1998, *Yeast*, 14:565–571.
Bullock, W.O. et al., 1987 *Biotechniques*, 5:376–378.
Dower, W.J. et al., 1988, *Nucleic Acids Res.*, 16:6127–6145.
Greener, A., 1993, *Strategies*, 6(1):7–9.
Greener, A., 1990, *Strategies*, 3:5–6.
Jerpseth, B. et al., 1992, *Strategies*, 5:81–83.
Miller, J., 1992, *A Short Course in Bacterial Genetics*, Cold Spring Harbor Press, 150–156.
Nielsen, P.E., 1999, *Current Opinion In Biotechnology*, 10:71–75.
Sokol, D.L. et al., 1998, *PNAS, USA*,, 95:11538–11543.
Stratagene Instruction Manual for Epicurian Coli® Electroporation–Competent Cells, 1997.

* cited by examiner

*Primary Examiner*—Remy Yucel
*Assistant Examiner*—Konstantina Katcheves
(74) *Attorney, Agent, or Firm*—Finnegan, Henderson, Farabow, Garrett & Dunner, LLP

(57) ABSTRACT

This invention provides methods for producing and selecting host cells that better survive transformation treatment by subjecting host cells to conditions that alter them, subjecting the altered cells to transformation conditions, and selecting host cells that survive the transformation conditions. This invention also provides methods for transferring nucleic acids of interest into host cells, using cells that are better able to survive transformation treatment. Also, this invention provides kits for producing or selecting host cells in transformation treatments, as well as, kits comprising various host cells that may be utilized in transformation experiments.

76 Claims, No Drawings

SELECTION FOR MORE EFFICIENT TRANSFORMATION HOST CELLS

RELATED APPLICATION INFORMATION

This application claims the filing date benefit of U.S. Provisional Patent Application Ser. No. 60/146,516, filed Jul. 30, 1999, which is incorporated by reference in its entirety for any purpose.

BACKGROUND AND SUMMARY OF THE INVENTION

The invention relates to the field of transformation of host organisms.

Introducing nucleic acids into *E. coli* and other host organisms is central to many types of experiments and analyses. For example, when searching for a gene of interest in a DNA library, the library must be transferred into a host organism. Since the DNA of many organisms is very complex, the number of independent clones that are needed to completely represent the organism is large. In order to make a library that completely represents the organism, the efficiency at which the DNA can enter the host cell becomes limiting. Optimizing this process facilitates the ability to create and screen DNA libraries.

a Similarly, for many other experimental approaches, the ability to introduce DNA into a host organism is the limiting factor. When cloning large segments of DNA for whole genome analysis (i.e., using bacterial artificial chromosomes), when performing PCR cloning (sometimes an inefficient process), or when carrying out random mutagenesis of a gene followed by cloning all potential altered forms, success often depends on the primary size of the initial transformation/electroporation pool. Again, by developing conditions that improve the process of introducing nucleic acids into any host organism, one increases the chance that the experiment will succeed.

There are several methods for introducing nucleic acids into host cells, e.g., incubating the host cells with co-precipitates of nucleic acids and Ca-phosphate (an example of chemical transformation) (Graham and van der Eb, *Virology* 52: 456–467 (1973)), directly injecting genes into the nucleus of the host cells (Diacumakos, *Methods in Cell Biology Vol.* 7, eds. Prescott, D. M. (Academic Press, 1973) pp. 287–311), introducing nucleic acids via viral vectors (Hamer and Leder, *Cell* 18: 1299–1302 (1979)), and using liposomes as a means of gene transfer (Fraley et al., *J. Biol. Chem.* 255: 10431–10435 (1980); Wong et al. *Gene* 10: 87–94 (1980)). Electroporation is another method for introducing nucleic acids into eukaryotic cells (Neumann et al. *Embo J.* 1: 841–845 (1982)). The method has also been used in transforming *E. coli* (Dower et al., *Nucleic Acids Research* 16: 6127–6145 (1988); Taketo, *Biochimica et Biophysica Acta* 949: 318–324 (1988)) and other bacteria (Chassy and Flickinger, *FEMS Microbiology Letters* 44: 173–177 (1987); Harlander, *Streptococcal Genetics*, eds. Ferretti and Curtiss (American Society of Microbiology, Washington, D.C. 1987) pp. 229–233).

Indeed, electroporation has become a typical method for transferring nucleic acids into a host organism. This method of transformation is generally performed by subjecting a host to a very strong electrical discharge, which typically kills a majority of cells. Only a small percentage survive. The process of electroporation is harsh and often results in the death of about 90% or more of the host organisms.

Electroporation involves the transfer of genes or fragments of nucleic acids into a host cell by exposure of the cell to a high voltage electric impulse in the presence of the genes or fragments (Andreason and Evans, *Biotechniques* 6: 650–660 (1988)). Quite often, the genes and fragments of nucleic acids are exogenous. If the cells survive the electroporation, it has been confirmed that over 90% of those cells will take up the nucleic acids. With this level of transfer, electroporation has been used to introduce genes or fragments of nucleic acids into host cells both permanently or transiently for short-term expression.

One typical electroporation protocol involves growing bacteria in rich media and concentrating them by washing in a buffer that contains 10% glycerol (Dower et al., 1988, U.S. Pat. No. 5,186,800). As discussed in U.S. Pat. No. 5,186,800, which is hereby incorporated by reference in its entirety, DNA is then added to the cells, and the cells are subjected to an electrical discharge, which disrupts the outer cell wall of the bacterium and allows DNA to enter the cell. The efficiency of transfer in *E. coli* varies depending on factors, including the genetic background of the *E. coli*. Routinely, an efficiency of $1\times10^9$ to $1\times10^{10}$ transformants per μg of input DNA may be achieved (XL-1Blue™ and XL10-Gold™, both cell lines from Stratagene).

A limitation on previous electroporation methods involving prokaryotic cells is that generally RecA-deficient cells are used. While RecA-deficient cells are stable host cells for transformation, cells expressing RecA show a high incidence of homologous recombination. Therefore, using RecA-expressing cells typically can cause problems with electroporation because the introduced nucleic acids would produce highly unstable transformants.

However, due to the deficiency, RecA-deficient cells do not survive the electroporation process as well as RecA-expressing cells. Therefore, those skilled in the art must choose between using RecA-deficient cells, which would be ideal for transformation experiments but often die before being transformed, and RecA-expressing cells, which survive transformation but typically produce unstable transformants. Despite the low survival rates, those of skill in the art typically use RecA-deficient cells.

Previous attempts to improve the electroporation process have involved methods used to prepare the cells, e.g., washing and centrifuging of cells during the processing stage and methods for applying the electrical shock, (e.g., different configuration of the apparatus that delivers the electrical pulse). The specific conditions that have been adjusted include, e.g., the concentration of nucleic acids, the temperature, the pulse decay time, and the initial field strength. Another attempt involves using different suspension materials to stabilize the cells in solution and assist in freezing them before the electrical treatment (Taketo 1988).

Another known method of introducing nucleic acids into a host organisms is by chemical treatment of the host organism. Typically, chemicals have been used to transfer nucleic acids into host cells, e.g., transfection. Known methods of chemically-mediated nucleic acid transfer are calcium phosphate-mediated transfection, and a variation, DEAE-dextran-mediated transfection (Sambrook et al. *Molecular Cloning: a laboratory manual*, $2^{nd}$ edition, eds. Sambrook et al. (Cold Spring Harbor Laboratory Press 1989)). Other chemically-mediated transformation methods include: 1) using polybrene to introduce the nucleic acids into cells that are resistant to other methods of transfection (Kawai and Nishizawa, *Mol. Cell Biol.* 4: 1172–1174 (1984); Chaney et al., *Somat. Cell Mol. Genet.* 12: 237–244 (1986)); 2) using polyethylene glycol to fuse protoplasts with cultured mammalian cells (Schaffner et al., *PNAS, USA*

77: 2163–2167 (1980); Rassoulzadegan et al., *Nature* 295: 257–259 (1982)); and 3) coating the nucleic acids of interest with a synthetic cationic lipid to introduce them into cells by fusion (Felgner et al., *PNAS, USA* 84: 7413–7417 (1987)).

According to certain embodiments, the present invention is directed to cells and methods of making cells that are more efficiently transformed in electroporation processes. The methods of the invention provide cells that are better able to survive and to be transformed than cells presently used in electroporation transformation methods.

As noted above, the process of electroporation according to known processes generally kills more than 90% of the host organisms (with the majority of the surviving cells taking up the DNA). According to certain embodiments of the invention, methods are provided in which host cells are altered and screened by exposing the altered cells to typical electroporation conditions. One selects altered cells that are able to survive the transformation conditions, e.g., electrical discharges. The selected altered cells have better viability after exposure to electroporation and are better suited to take up nucleic acids by electroporation. Thus, the altered cells have better transformation efficiency.

Using a similar methodology as noted above for increasing the viability of host cells after exposure to electroporation, according to certain embodiments, the invention provides methods for improving the transformation efficiency of host cells by selecting for or producing host cells that survive other types of transformation conditions, e.g., chemical treatment. Thus, according to certain embodiments of the invention, methods are provided in which cells are altered and exposed to chemically-mediated nucleic acid transfer conditions. Cells that survive such conditions have better transformation efficiency.

In certain embodiments, the cells are altered by mutation.

In certain embodiments, the host cells may include prokaryotic or eukaryotic cells.

This invention also provides various methods for selecting host cells better able to survive transformation treatment, which generally includes subjecting host cells to conditions that identify cells that survive the transformation conditions and isolating the identified host cells. Thus, host cells better able to survive transformation treatment are selected.

This invention also provides host cells produced or selected by the above-identified methods. And, this invention provides specific bacterial strains that have higher transformation efficiency than those typically used.

According to certain embodiments, methods are provided for transferring nucleic acids of interest into host cells by combining host cells produced or selected by the above-described methods with nucleic acids of interest and subjecting the host cells to transformation conditions to transfer the nucleic acids of interest into the host cells.

In certain embodiments, this invention further comprises culturing the transformed cells in a selected media capable of promoting their growth.

This invention also provides a kit for use in the practice of the above-described methods.

This invention also provides a kit comprising host cells that have been produced or selected by the above-described methods, as well as specific bacterial strains that have higher transformation efficiencies.

DETAILED DESCRIPTION OF EMBODIMENTS OF THE INVENTION

This invention provides various methods for producing host cells that better survive transformation treatment, which generally includes subjecting host cells to conditions that alter them, subjecting the altered host cells to transformation conditions, and selecting host cells that survive the transformation conditions.

One can use both prokaryotic and eukaryotic host cells to practice the invention unless specified otherwise. Suitable host cells according to certain embodiments are disclosed in Sambrook et al. *Molecular Cloning: a laboratory manual, $2^{nd}$ edition*, eds. Sambrook et al. (Cold Spring Harbor Laboratory Press 1989). In certain embodiments, the host cells are prokaryotic, including, but not limited to, bacterial cells. One skilled in the art would know which bacterial cells would be appropriate in practicing this invention. In certain embodiments of the invention, one uses gram-negative bacterial cells. In certain preferred embodiments, the gram-negative bacterial cells are *E. coli*. In certain embodiments, the bacterial cell strain is XL1-Blue MRF'™ (Stratagene Catalogue). In certain embodiments, the bacterial cell strain is XL10-Gold™ (Stratagene Catalogue).

As used herein, the term "transformation conditions" includes various conditions used for transferring nucleic acids into host cells. Those conditions would be any conditions that put cells under various stresses. When one makes or selects host cells that are better able to survive transformation treatment according to certain embodiments, one subjects the cells to transformation conditions, but does not include nucleic acid of interest to be transformed into the cells. Only after such cells have been selected would one employ nucleic acids to actually obtain transformed host cells.

When transformation is the goal, the transfer DNA may reside transiently or as a stable extrachromosal element, e.g., plasmid, or may be integrated into the host cell's genome. Certain embodiments include use of electricity to treat the cells so that nucleic acids may enter cells. A specific example of electrical transformation conditions is electroporation. Electroporation and procedures for carrying it out are well-known in the art (see e.g., Sambrook et al. 1987; Stratagene Instruction Manual for *Epicurian Coli*® Electroporation-Competent Cells 1997). Conditions for optimal efficiency can be determined by one skilled in the art. In certain embodiments, during electroporation, the cells are exposed to about 1.75 kV and 200 ohms in a 0.1 cm cuvette. In certain embodiments, during electroporation, the cells are exposed to about 2.5 kV and 1000 ohms in a 0.2 cm cuvette. Other electrical treatments may be used in conjunction with this method.

Other transformation conditions include subjecting cells to particular chemical conditions that allow nucleic acids to enter the cells. Chemically-mediated nucleic transfer methods are well-known in the art. (See, e.g., Sambrook et al. *Molecular Cloning: a laboratory manual, $2^{nd}$ edition*, eds. Sambrook et al. (Cold Spring Harbor Laboratory Press 1989)). According to certain embodiments, one can use $Ca^{2+}$-phosphate precipitation of nucleic acids and incubation with host cells. Other methods include, but are not limited to, polybrene-mediated transfection, chemically-mediated fusion of cell membranes of protoplasts with mammalian cells, and chemically-coated nucleic acids fused with cell membranes.

Various methods and various transformation conditions are contemplated for use in this invention, and one skilled in the art would know how to practice the present invention using any of these methods or modifications of them. Moreover, since embodiments of the present invention are directed to general methods of selecting cells that survive transformation conditions, methods according to this invention can employ any conditions that result in transformed cells. Thus, the invention may be used with transformation conditions that are developed in the future.

In order to produce cells that better survive transformation treatment, the cells are subjected to various conditions that alter the cells. The term "alter" encompasses any change in the cells. Such conditions may include, but are not limited to, mutating the host cells. Many methods exist for making mutant cells. (See, e.g., J. Miller, A *Short Course In Bacterial Genetics*, Cold Spring Harbor Press (1992)). These methods include, but are not limited to, subjecting cells to ionizing radiation, subjecting cells to chemical mutagens, and/or subjecting cells to compounds that compromise growth and induce mutagenic repair pathways. According to certain embodiments, one may use a host strain that exhibits a high spontaneous mutation rate or that is known to be highly susceptible to mutagens, to obtain a large pool of mutated host cells. In addition, growth of a nonmutagenized host can yield spontaneous mutants with the desired properties, e.g., naturally occurring mutations.

Typical chemical mutagens that may be used to produce mutants include, but are not limited to, nitrous acid, hydroxylamine (HA), ethylmethanesulfonate (EMS), or nitrosoguanidine (NTG). One skilled in the art would know the appropriate mutagens to use to make mutant host cells.

If the mutagenesis is by radiation, in certain embodiments, the irradiation includes, but is not limited to, ultraviolet irradiation, microwave irradiation, and/or gamma irradiation. One skilled in the art would know how to determine the dosage to use to mutate the cells of interest. In certain embodiments, the radiation would be at a dose such that 90 to 95% of the host cells would die after exposure. The surviving cells would then be subjected to the transformation conditions. In *E. coli*, according to certain embodiments, a preferred amount would be 150 $\mu$J.

In certain embodiments, the host cells transiently express Rec A protein. Certain methods to obtain cells that transiently express RecA protein include transfecting a RecA-deficient bacterial cell with nucleic acids that encode Rec A protein, e.g., transfection with a plasmid carrying the gene that encodes Rec A protein. Such transfected cells typically survive mutating conditions, specifically irradiation, better than non-transfected Rec A-deficient cells. In certain embodiments, the cells will become Rec A-deficient after being mutated or after the selection process following exposure to transformation conditions. Thus, they will be Rec A-deficient prior to use in actual transformation methods with nucleic acids of interest.

To select cells that better survive transformation conditions, one selects cells that survive after exposure to such conditions. As described above, if the cells survive the transformation conditions during the selection procedures, those cells have a high likelihood of being transformed with nucleic acids of interest when exposed to such transformation conditions with such nucleic acids.

In certain embodiments, one may use the selection process with cells that have been subjected to conditions that alter the cells. In certain embodiments, the selection process can be used with any cells, even if they have not been subjected to any particular altering conditions. In any event, one uses the selection process to select cells that better survive transformation treatment. That ability to better survive transformation treatment may arise without subjecting the cells to conditions that alter the cells, e.g., by spontaneous mutation, and the selection process allows one to select such cells from other cells that do not survive the process.

Also, one skilled in the art would know how to select an appropriate media to promote growth of altered cells produced by the above-described methods. The media should propagate the altered cells such that they retain the mutations created by those conditions. See J. Miller, A *Short Course In Bacterial Genetics*, Cold Spring Harbor Press (1992) for examples of suitable media and growth conditions. Further, after subjecting the host cells to transformation conditions, the media should also promote the growth of the surviving host cells.

Accordingly to certain embodiments, one subjects the host cells to at least two rounds of conditions that alter them and/or to at least two rounds of transformation conditions. In other words, one may use multiple exposures to altering conditions and/or multiple exposures to transformation conditions. In certain embodiments, one may alternate between altering conditions and transformation conditions.

This invention also provides methods for selecting host cells that better survive transformation treatment, which includes obtaining host cells that have been altered, subjecting the host cells to transformation conditions, and then selecting host cells that survive the transformation conditions.

In view of the present disclosure, one skilled in the art can select cells that survive transformation conditions by subjecting the cells to those conditions, such as electroporation conditions and other transformation methods. Because the surviving cells have a demonstrated resistance to the transformation conditions, more of the selected cells can survive the transformation conditions with nucleic acids of interest and accordingly, more cells will be transformed.

This invention also provides host cells that are either produced or selected by the above-identified methods. In certain embodiments, the host cells can be prokaryotic or eukaryotic. Further, in certain embodiments, the host cells are *E. coli*.

According to certain embodiments, the host cells are *Escherichia coli* XL1-Blue MRF'B150 assigned ATCC No. PTA-369, which were deposited on Jul. 16, 1999, at the American Type Culture Collection, 10801 University Blvd., Manassas, Va. 20110-2209.

This invention also provides methods for transferring nucleic acids of interest into host cells, including combining host cells produced or selected by the above-described methods with the nucleic acids of interest, subjecting the host cells to transformation conditions, and then selecting the host cells that survive the transformation conditions and have the nucleic acids of interest transferred into them.

As used herein, the term "nucleic acids of interest" includes, but is not limited to, fragments of nucleic acid sequences, full length nucleic acid sequences that encode functional or non-functional proteins, polynucleotides, or oligonucleotides. The nucleic acids of interest may be obtained naturally or synthetically, e.g., using PCR or mutagenesis. Further, the nucleic acids may be circular, linear, or supercoiled in their topology. According to certain embodiments, linear strains of nucleic acid are preferred. The nucleic acids of interest also include single stranded RNA, double stranded RNA, and mRNA.

The term "nucleic acids of interest" also may include derivatives of nucleic acids or modified nucleic acids. Modified nucleic acids include nucleic acids to which an organic and/or an inorganic moiety has been attached. The attachment can be covalent or noncovalent. Such nucleic acids may be modified by attaching various chemical compounds to a terminal or medial portion, e.g., methylated nucleic acids, molecular beacons, or PNAs (Sokol, D. L. et al., *PNAS, USA*, 95:11538–11543 (1998); Nielsen, P. E., *Current Opinion In Biotechnology*, 10:71–75 (1999)). As used herein "PNA" is a modified nucleic acid that has a peptide attached to the nucleic acid. Thus, the term "peptide nucleic acid" also is used to refer to PNAs. Such modified nucleic acids are well known to those of skill in the art (Nielsen 1999).

Although not limited to such sizes, certain embodiments typically employ nucleic acids of interest ranging from about 2.5 kb to about 1000 kb (including any point between about 2.5 kb and about 1000 kb, depending on a number of factors. One skilled in the art would have the knowledge to determine the optimal length or cell line and would be able to determine other optimal factors for transformation.

As used herein, the term "host cells that contain the nucleic acids of interest" may include host cells that include transiently transferred or permanent or stably integrated nucleic acids of interest. One skilled in the art would be able to determine the optimal conditions to transfer the nucleic acids of interest, e.g., length of nucleic acids or pulse time.

According to certain embodiments, this invention also provides kits used in the practice of the above-described methods. For example, in certain embodiments the kits can be used to produce or select cells that better survive transformation conditions. The kits may include host cells, materials for altering the cells, materials for subjecting the cells to transformation conditions, and/or instructions to carry out the methods.

In certain embodiments, this invention also provides kits that include host cells that have been produced or selected by the methods described. In certain embodiments, these kits could be used in producing libraries, including genomic and cDNA libraries. Because these kits would include host cells that have a higher transformation efficiency (a greater number of the host cells will survive the transformation process), one skilled in the art could produce libraries more efficiently.

Certain embodiments of the invention are described in the following examples. However, these examples are offered solely for the purpose of illustrating the invention, and should not be interpreted as limiting the invention in any way.

EXAMPLE

1. Enrichment for Mutants that Are Better Hosts for Electroporation a. Selection of mutant cells that are resistant to electric charges A plasmid, pJC859 (gift from John Clark at U.C. Berkeley) that expresses the *E. coli* Rec A gene product was introduced extrachromosomally into the *E. coli* strains, XL10-Gold™ and XL1-Blue MRF'™. Both XL10-Gold™ and XL1-Blue MRF'™ are *E. coli* Rec A-deficient strains. Transformation conditions are discussed in Stratagene's Instruction Manual for *Epicurian Coli*® Electroporation-Competent Cells 1997. Rec A-deficient strains are extremely sensitive to UV light and therefore, only a few cells typically would survive irradiation treatment. Therefore, these Rec-A deficient strains were transiently transfected with a plasmid that expresses the RecA gene product to increase the number of cells that mutated and survived.

The transiently transformed cells were treated with UV radiation by standard protocol (J. Miller, A *Short Course In Bacterial Genetics*, Cold Spring Harbor Press, pp. 150–156 (1992)). The following changes from the described Miller method were used. First, a UV crosslinker (Stratalinker) was used rather than a germicidal lamp. Second, plastic Petri dishes were used rather than glass dishes. Third, instead of 0.1 M $MgSO_4$ buffer, the SM buffer was used (50 mM Tris pH 7.5, 100 mM NaCl, 10 mM $MgSO_4$, 0.01% gelatin). Surviving UV-irradiated cells were grown and subjected to the following procedures.

Fermentation and Inoculation

A 15 liter Applikon™ fermenter was thoroughly cleaned with reverse osmosis water. After cleaning, liquid remaining in the fermenter was removed to provide an ion-free environment. Specifically, all traces of magnesium were removed from the fermenter. Media to grow the *E. coli* was produced in the glass vessel of the fermenter by adding 240–280 grams DIFCO™ tryptone, 60–70 grams of DIFCO™ yeast, and 6 grams of NaCl to the empty vessel. Twelve liters of 0.2 micron filtered water was added to the fermenter. The fermenter was autoclaved on slow exhaust for 35–45 minutes and cooled. After removing the fermenter from the autoclave, it was heated up to 37° C.

The surviving irradiated XL1-Blue MRF™ and XL10-Gold™ sample from the work above was streaked out on Tet plates and incubated at 37° C. for 24 hours (Sambrook et al. 1987). (If different types of cells are used, one skilled in the art would know appropriate plates and conditions for growth.)

Under sterile conditions, 75–100 ml of magnesium-free SOB (20 grams Tryptone, 5 grams yeast extract, and 0.5 grams of NaCl per liter) was poured into three sterile 250 ml flasks. Two to five bacterial colonies, between 2–5 mm in width, were chosen and inoculated into the magnesium-free SOB. The cells were grown overnight at room temperature in an air shaker at 250–275 rpm.

The optical density (O.D.) of the cells cultured overnight was determined with a Beckman DU640B spectrometer by diluting the cells 1 to 10, i.e., 900 $\mu l$ of media was added to a quartz cuvette, the spectrometer was zeroed with the media-filled cuvette, 100 $\mu l$ of cells was added to the cuvette, and the O.D. of the cells was determined.

Under sterile conditions, 60–100 O.D. units of the cells were added into the fermenter using an electric pump. The temperature of the fermenter was maintained at 37° C. (The temperature to set the fermenter may vary depending on the type of cells that are used. Those skilled in the art know how to determine the optimal conditions for growing different bacterial cells in a fermenter.)

When the O.D. of the fermenter is 0.15–0.25 or when it was no longer possible to see through the fermenter, as much SOB as the fermenter would hold and 1–2 drops of sterile anti-foam A™ (Sigma) were added. To maintain oxygen content, the culture was agitated with airing. The fermentation process took about five hours. One skilled in the art could easily determine the optimal conditions and time frame for harvesting the cells.

At the desired final O.D. 0.82 [Beckman DU640B spec 550 nm], the fermenter was cooled to 4° C. The bacteria was concentrated to 0.5 liters with a mini-sert crossflow filtration unit from Sartorious. When the fluid level inside the fermenter was 0.75 liters, a buffer exchange was set up. The buffer exchange was run until 2.0 gallons of sterile cooled water (4° C.) had been exchanged. Another buffer exchange was run with 1.0 gallon of pre-cooled 0.2 micro filtered water + 15% glycerol and 2.4% sorbitol.

Afterwards, the cells were removed from the fermenter. The cells were split into 2 spin buckets and centrifuged (Sorval Centrifuge™) for 15 minutes at 4,000 rpm at 0° C. The supernatent was decanted. 35 ml of 15% glycerol/water containing 2.4% sorbitol was poured into the spin buckets and the pellets were pipetted into solution as quickly as possible. After solubilizing the pellet, the solutions were combined into one spin bucket.

Using the XL10-Gold™ cells from the processes above, the cells were tested in various trials for their ability to survive electroporation. Pools of the indicated cells were then exposed to a second, and sometimes, third round of electroporation to ultimately obtain cells with higher transformation efficiency. Transformation efficiency was determined by addition of 10 picograms of pUC 18 DNA and counting colony forming units obtained. (See Stratagene's Instruction Manual for *Epicurian Coli®* Electroporation-Competent Cells 1997, which instructs one skilled in the art how such calculations are made.)

The cells were electroporated under standard conditions for pUC 18 at 1.75 kV and 200 ohms in a 0.1 cm cuvette to test for survival. Their transformation efficiencies were also tested under the same conditions.

TRIAL #1

| Dilution of cells | colonies before electroporation | colonies after electroporation | % survival |
|---|---|---|---|
| $10^{-3}$ | confluent | confluent (#1) | |
| $10^{-4}$ | confluent | $>10^4$ (#2) | |
| $10^{-5}$ | confluent | 1000 | |
| $10^{-6}$ | $10^4$ | 148 | 1.5 |
| $10^{-7}$ | 1000 | 18 | 1.8 |

Cells from colonies #1 and #2 were pooled and the process was repeated using identical electroporation conditions. If mutants were present, it was believed that a proportion of cells surviving the electroporation process should increase. In the following trials, the best mutants (indicated in bold) were pooled and chosen for further enrichment and further testing, again using identical electroporation conditions.

TRIAL #2

Pool #1

| Dilution of cells | colonies before electroporation | colonies after electroporation | % survival |
|---|---|---|---|
| $10^{-3}$ | confluent | confluent | |
| $10^{-4}$ | confluent | $>10^4$ | |
| $10^{-5}$ | confluent | 3000 (#A) | |
| $10^{-6}$ | $>10^4$ | 500 | 2.0 |
| $10^{-7}$ | 1500 | 80 | 2.0 |

Pool #2

| Dilution of cells | colonies before electroporation | colonies after electroporation | % survival |
|---|---|---|---|
| $10^{-3}$ | confluent | confluent | |
| $10^{-4}$ | confluent | confluent | |
| $10^{-5}$ | confluent | $>10^4$ | |
| $10^{-6}$ | $>10^4$ | 1000 (#2B) | |
| $10^{-7}$ | 3000 | 150 | 5.0 |

TRIAL #3

Pool #1A (From Pool #1 Above)

| Dilution of cells | colonies before electroporation | colonies after electroporation | % survival |
|---|---|---|---|
| $10^{-3}$ | confluent | confluent | |
| $10^{-4}$ | confluent | confluent | |
| $10^{-5}$ | confluent | $10^4$ | |
| $10^{-6}$ | $>10^4$ | 1000 (#1A1) | |
| $10^{-7}$ | 1000 | 90 (#1A2) | 9.0 |

Pool #2B (From Pool #2 Above)

| Dilution of cells | colonies before electroporation | colonies after electroporation | % survival |
|---|---|---|---|
| $10^{-3}$ | confluent | confluent | |
| $10^{-4}$ | confluent | confluent | |
| $10^{-5}$ | confluent | $>10^4$ | |
| $10^{-6}$ | $>10^4$ | 500 (#2B1) | |
| $10^{-7}$ | 1000 | 52 (#2B2) | 5.2 |

Pool #1A1 (From Pool #1A Above)

| Dilution of cells | colonies before electroporation | colonies after electroporation | % survival |
|---|---|---|---|
| $10^{-4}$ | confluent | $>10^4$ | |
| $10^{-5}$ | confluent | 2500 | |
| $10^{-6}$ | confluent | 500 | |
| $10^{-7}$ | 500 | 44 | |
| $10^{-8}$ | 66 | 6 | 8.8 |

Pool #1A2 (Fom Pool #1A Above)

| Dilution of cells | colonies before electroporation | colonies after electroporation | % survival |
|---|---|---|---|
| $10^{-4}$ | confluent | $>10^4$ | |
| $10^{-5}$ | confluent | 2500 | |
| $10^{-6}$ | confluent | 400 | |
| $10^{-7}$ | 500 | 58 | 11.6 |
| $10^{-8}$ | 75 | 4 | |

Pool #2B1 (From Pool #2B Above)

| Dilution of cells | colonies before electroporation | colonies after electroporation | % survival |
|---|---|---|---|
| $10^{-4}$ | confluent | $>10^4$ | |
| $10^{-5}$ | confluent | 2500 | |
| $10^{-6}$ | confluent | 500 | |
| $10^{-7}$ | 1000 | 60 | 6.0 |
| $10^{-8}$ | 200 | 4 | |

| Pool #2B2 (From Pool #2B Above) | | | |
| --- | --- | --- | --- |
| Dilution of cells | colonies before electroporation | colonies after electroporation | % survival |
| $10^{-4}$ | confluent | $>10^4$ | |
| $10^{-5}$ | confluent | 5000 | |
| $10^{-6}$ | confluent | 500 | |
| $10^{-7}$ | 1000 | 44 | 4.4 |
| $10^{-8}$ | 130 | 5 | |

| Individual Colonies from Pool #1A2 | | |
| --- | --- | --- |
| 1A2 EC1 | 8.0% | viability after transformation |
| 1A2 EC2 | 2.0% | viability after transformation |
| 1A2 EC3 | 9.8% | viability after transformation |
| 1A2 EC4 | 14.0% | viability after transformation |

The individual colonies from Pool #1A2 were then subjected to same transformation conditions as discussed above, which resulted in 1A2 EC1; 1A2 EC2; 1A2 EC3; and 1A2 EC4. Comparing the transformation efficiency of XL10-Gold™ at $1.0 \times 10^9$ cfu/μg pUC DNA with the transformation efficiency of 1A2 EC4 Prep #1 at $1.7 \times 10^{10}$ cfu/μg pUC DNA demonstrates an increase in efficiency.

In another series of experiments, the parental XL10-Gold™ strain survived electroporation around 0.2%, while the 1A2 EC4 strain survived around 2.0%. The same electroporation conditions were used as those discussed above. The transformation efficiencies of the two strains were $4.0 \times 10^8$ versus $5.0 \times 10^9$ respectively (a 12.5 fold increase).

Accordingly, cells that survived at a higher rate, also efficiently transformed.

Similar enrichment trials were run on XL1-Blue MRF'™ cells that were mutated, electroporated, and then tested with nucleic acid transformers. The host cells subjected to mutation and growth conditions above were exposed to 2.0 kV and 200 ohms to test for survival. A mutant cell line, XL1-Blue MRF' B150, was selected from these experiments. Whereas XL-1Blue MRF' had a survival rate of 2.2%, the mutant cell line had a survival rate of 12.8%. More importantly, the transformation efficiency showed an increase of over 3.5 fold. The efficiency of the parent strain was $8.0 \times 10^9$ and the efficiency of the mutant strain was $3.0 \times 10^{10}$.

All documents mentioned in this application, including but not limited to, articles, books, reviews, patents and patent applications, are hereby incorporated by reference in their entirety into this specification.

REFERENCES

1. Bower, W. J. et al. (1988) *Nucleic Acids Res.* 16:6127–6145.
2. Greener, A. (1993) *Strategies* 6(1):7–9.
3. Greener, A. (1990) *Strategies* 3:5–6.
4. Bullock, W. O. et al. (1987) *Biotechniques* 5:81–83.
5. Jerpseth, B. et al. (1992) *Strategies* 5:81–83.
6. Nielsen, P. E. (1999) *Current Opinion In Biotechnology* 10:71–75.
7. Sokol, D. L. et al. (1998) *PNAS, USA* 95: 11538–11543.

What is claimed is:

1. A method for producing an altered cell line that better survives transformation treatment than unaltered host cells, comprising:

(a) subjecting host cells to conditions that alter at least a portion of the host cells, wherein the conditions that alter the hosts cells are mutation conditions that mutate at least one of the host cells;

(b) subjecting the altered host cells of (a) to transformation conditions;

(c) selecting altered host cells of (b) that survive the transformation conditions; and (d) growing the selected host cells from (c) to generate an altered cell line that better survives transformation treatment than unaltered host cells.

2. The method of claim 1, wherein the host cells are prokaryotic or eukaryotic.

3. The method of claim 2, wherein the host cells are prokaryotic.

4. The method of claim 3, wherein the prokaryotic cells are *E. coli*.

5. The method of claim 1, wherein the transformation conditions include electrical treatment.

6. The method of claim 5, wherein the electrical treatment is electroporation.

7. The method of claim 6, wherein the electroporation comprises treating the host cells to about 1.75 kV and 200 ohms.

8. The method of claim 6, wherein the electroporation comprises treating the host cells to about 2.5 kV and 1000 ohms.

9. The method of claim 1, wherein the transformation conditions include chemical treatment.

10. The method of claim 9, wherein the chemical treatment is $Ca^{2+}$-phosphate precipitation.

11. The method of claim 1, wherein the host cells are mutated by chemical mutagens.

12. The method of claim 1, wherein the host cells are mutated by irradiation.

13. The method of claim 12, wherein the irradiation comprises ultraviolet irradiation.

14. The method of claim 1, wherein the host cells transiently express Rec A protein prior to subjecting the host cells to conditions that alter them in (a), such that Rec A protein is present in the host cells during (a).

15. The method of claim 1, wherein the host cells are subjected at least twice to conditions that alter them.

16. The method of claim 1, wherein the host cells are subjected at least twice to transformation conditions.

17. The method of claim 1, further comprising culturing the selected host cells of (c) in a selected media capable of promoting their growth.

18. A method for producing an altered cell line that better survives transformation treatment than unaltered host cells, comprising:

(a) obtaining host cells that have been altered, wherein the hosts cells have been altered by mutation conditions that mutate at least one of the host cells;

(b) subjecting the altered host cells of (a) to transformation conditions;

(c) selecting altered host cells of (b) that survive the transformation conditions; and (d) growing the selected host cells from (c) to generate an altered cell line that better survives transformation treatment than unaltered host cells.

19. The method of claim 18, wherein the host cells are prokaryotic or eukaryotic.

20. The method of claim 19, wherein the prokaryotic cells are *E. coli*.

21. The method of claim 18, wherein the transformation conditions include electrical treatment.

22. The method of claim 21, wherein electrical treatment is electroporation.

23. The method of claim 22, wherein the electroporation comprises treating the host cells to about 1.75 kV and 200 ohms.

24. The method of claim 22, wherein the electroporation comprises treating the host cells to about 2.5 kV and 1000 ohms.

25. The method of claim 18, wherein the transformation conditions include chemical treatment.

26. The method of claim 25, wherein the chemical treatment comprises $Ca^{2+}$-phosphate precipitation.

27. The method of claim 18, wherein the host cells are mutated by chemical mutagens.

28. The method of claim 18, wherein the host cells are mutated by irradiation.

29. The method of claim 28, wherein the irradiation comprises ultraviolet irradiation.

30. The method of claim 18, wherein the host cells transiently express Rec A protein prior to subjecting the host cells to conditions that alter them in (a), such that Rec A protein is present in the host cells during (a).

31. The method of claim 18, wherein the host cells are subjected at least twice to conditions that alter them.

32. the method of claim 18, wherein the host cells are subject at least twice to transformation conditions.

33. The method of claim 18, further comprising culturing the selected host cells of (c) in a selected media capable of promoting their growth.

34. An altered cell line produced by the method of claim 1.

35. The altered cell line of claim 34, wherein the cells are prokaryotic or eukaryotic.

36. The altered cell line of claim 35, wherein the prokaryotic cells are E. coli.

37. An altered cell line produced by the method of claim 18.

38. The altered cell line of claim 37, wherein the cells are prokaryotic or eukaryotic.

39. The altered cell line of claim 38, wherein the prokaryotic cells are E. coli.

40. A bacterial strain designated XL1-Blue MRF' B150.

41. A method for producing a cell line that better survives transformation treatment that unselected host cells, comprising:
  (a) subjecting host cells to transformation conditions;
  (b) selecting host cells of (a) that survive the transformation conditions; and
  (c) growing the selected host cells from (b) to generate a cell line that better survives transformation treatment than unselected host cells.

42. The method of claim 41, wherein the host cells subjected to transformation conditions are cells in which a spontaneous mutation has occurred.

43. A method for transferring nucleic acids of interest into cells of an altered cell line, comprising:
  (a) combining cells from an altered cell line produced by the method of claim 11 with nucleic acids of interest;
  (b) subjecting the cells and nucleic acids of (a) to second transformation conditions, wherein the second transformation conditions may be the same as or different from the transformation conditions employed to produce the altered host cells; and
  (c) selecting cells of (b) that survive the transformation conditions and that contain the nucleic acids of interest.

44. The method of claim 43, further comprising culturing the cells transformed in (c) in a selected media capable of promoting their growth.

45. The method of 43, wherein cells are prokaryotic or eukaryotic.

46. The method claim 45, wherein the prokaryotic cells are E coli.

47. The method of claim 43, wherein the second transformation conditions include electrical treatment.

48. The method of claim 42, wherein the electrical treatment is electroporation.

49. The method of claim 43, wherein the second transformation conditions include chemical treatment.

50. The method of claim 49, wherein the chemical treatment is $Ca^{2+}$-phosphate precipitation.

51. The method of claim 43, wherein the nucleic acids of interest are molecular beacons.

52. The method of claim 43, wherein the nucleic acids of interest are peptide nucleic acids.

53. The method of claim 43, wherein the nucleic acids of interest are single-stranded RNA.

54. The method of claim 43, wherein the nucleic acids of interest are double-stranded RNA.

55. The method of claim 43, wherein the nucleic acids of interest are modified nucleic acids.

56. A method for transferring nucleic acids of interest into cells from an altered cell line, comprising:
  (a) combining cells from an altered cell line produced by the method of claim 18 with nucleic acids of interest;
  (b) subjecting the cells and nucleic acids of (a) to transformation conditions, wherein the second transformation conditions may be the same as or different from the transformation conditions employed to produce the altered host cells; and
  (c) selecting cells of (b) that survive the transformation conditions and that contain the nucleic acids of interest.

57. The method of 56, further comprising culturing the cells transformed in (c) in a selected media capable of promoting their growth.

58. The method of 56, wherein cells are prokaryotic or eukaryotic.

59. The method claim 58, wherein the prokaryotic cells are E. coli.

60. The method of claim 56, wherein the second transformation conditions include electrical treatment.

61. The method of claim 60, wherein the electrical treatment is electroporation.

62. The method of claim 56, wherein the second transformation conditions include chemical treatment.

63. The method of claim 62, wherein the chemical treatment is $Ca^{2+}$-phosphate precipitation.

64. The method of claim 56, wherein the nucleic acids of interest are molecular beacons.

65. The method of claim 56, wherein the nucleic acids of interest are peptide nucleic acids.

66. The method of claim 56, wherein the nucleic acids of interest are nucleic acids that are modified by a chemical covalent linkage.

67. A method for transferring nucleic acids of interest into cells, comprising:
  (a) combining cells of a cell line produced by the method of claim 41 with nucleic acids of interest;
  (b) subjecting the cells and nucleic acids of (a) to transformation conditions, wherein the second transformation conditions may be the same as or different from the transformation conditions employed to produce the altered host cells; and
  (c) selecting cells of (b) that survive the transformation conditions and that contain the nucleic acids of interest.

68. A kit comprising an altered cell line produced by the method of claim 1.

69. A kit comprising an altered cell line produced by the method of claim 18.

70. The kit of claim 68, further comprising materials for subjecting the cells to transformation conditions.

71. The kit of claim 69, further comprising materials for subjecting the cells to transformation conditions.

72. A kit comprising host cells from the altered cell line of claim 34.

73. A kit comprising host cells from the altered cell line of claim 37.

74. A kit comprising the bacterial strain of claim 40.

75. A kit comprising a cell line produced by the method of claim 41.

76. The kit of claim 75, further comprising materials for subjecting the cells to transformation conditions.

* * * * *